United States Patent [19]

Torp et al.

[11] Patent Number: 5,560,363

[45] Date of Patent: Oct. 1, 1996

[54] METHOD FOR CALCULATION OF BLOOD VELOCITY AND BLOOD VELOCITY SPREAD FROM MULTI GATED DOPPLER SIGNALS

[75] Inventors: Hans Torp, Trondheim; Kjell Kristoffersen, Oslo, both of Norway

[73] Assignee: Vingmed Sound A/S, Horton, Norway

[21] Appl. No.: 379,208

[22] Filed: Jan. 27, 1995

[30] Foreign Application Priority Data

Dec. 7, 1994 [NO] Norway ..................................... 944736

[51] Int. Cl.$^6$ ...................................................... A61B 8/06
[52] U.S. Cl. ............................................................ 128/661.09
[58] Field of Search ........................... 128/661.07–661.1; 73/861.25

[56] References Cited

U.S. PATENT DOCUMENTS

| | | | |
|---|---|---|---|
| 4,803,990 | 2/1989 | Bonnefous et al. | 128/661.08 |
| 4,930,513 | 6/1990 | Mayo et al. | 128/661.09 |
| 5,081,994 | 1/1992 | Hassler | 128/661.09 |
| 5,386,830 | 2/1995 | Powers et al. | 128/661.09 |
| 5,429,137 | 7/1995 | Phelps et al. | 128/661.09 |

OTHER PUBLICATIONS

Zrnic, "Spectral Moment Estimates from Correlated Pulse Pairs" *IEEE Transactions on Aerospace and Electronic Systems*, vol. AES–12, No. 4 July 1977, pp. 344–354.

Kasai et al., "Real–Time Two–Dimensional Blood Flow Imaging Using an Autocorrelation Technique" *IEEE Transactions on Sonics and Ultrasonics*, vol. SU–32, No. 3, May 1985, 458–464.

Bonnefous et al., "Time Domain Formulation of Pulse–Doppler Ultrasound and Blood Velocity Estimation by Cross Correlation" *Ultrasonic Imaging* 8, (1986), pp. 73–85.

Ferrara et al., "A New Wideband Spread Target Maximum Likelihood Estimator for Blood Velocity Estimation—Part I: Theory" *IEEE Transactions on Ultrasonics, Ferroelectrics, and Frequency Control*, vol. 38, No. 1, Jan. 1991, pp. 1–26.

Ferrara et al., "The Effect of Frequency Dependent Scattering and Attenuation on the Estimation of Blood Velocity Using Ultrasound" *IEEE Transactions on Ultrasonics, Ferroelectrics, and Frequency Control*, vol. 39, No. 6, Nov. 1992, pp. 754–767.

Wilson, "Description of Broad–Band Pulsed Doppler Ultrasound Processing Using the Two–Dimensional Fourier Transform" *Ultrasonic Imaging*, vol. 13, (1991) pp. 301–315.

*Primary Examiner*—Francis Jaworski
*Attorney, Agent, or Firm*—Rothwell, Figg, Ernst & Kurz, P.C.

[57] ABSTRACT

A method for velocity estimation based on a complex demodulated doppler signal in a multi-gated doppler. The method is based on the autocorrelation function estimates of the complex demodulated doppler signal. Contribution to the correlation function from the receiver noise is found by measuring the noise in absence of echo signals. The obtained values are subtracted from the correlation estimates before further processing. A limited number of candidates for the true velocity are calculated from the autocorrelation function phase.

4 Claims, 2 Drawing Sheets

METHOD FOR CALCULATION OF BLOOD VELOCITY AND BLOOD VELOCITY SPREAD FROM MULTI GATED DOPPLER SIGNALS

FIELD OF THE INVENTION

The present invention relates to diagnostic ultrasound systems which measure the flow of fluids through Doppler interrogation, and more particularly to signal processing methods for calculation of blood velocity field parameters, to be used in ultrasonic color flow imaging systems.

BACKGROUND OF THE INVENTION

In 2D ultrasound Doppler blood flow imaging, the signal power, velocity, and velocity spread are calculated from autocorrelation estimates of the received echo signal in each point of the image, and coded into colors for display. A corresponding technique is referred to as 'correlated pulsed pair' in Weather radar applications as discussed in D. S. Zrni'c, "Spectral moment estimates from correlated pulsed pair" *IEEE Trans. on Aerosp. Electron.*, vol. AES-13. pp. 344–354, 1977. It was first applied to ultrasound blood velocity measurement as discussed in C. Kasai, K. Namekawa, A. Koyano, and R. Omoto, "Real-Time Two-Dimensional Blood Flow Imaging Using an Autocorrelation Technique" *IEEE Trans. Sonics Ultras.*, vol. SU-32, pp. 458–464, 1985, under the name 'autocorrelation method'. A severe limitation of this technique is the velocity ambiguity problem, which occurs when the Doppler shift frequency exceeds the Nyquist limit at half the repetition frequency of the transmitted pulses. Several methods have been proposed to partly overcome this problem.

Time delay estimation from pulse to pulse by cross correlation technique was applied to ultrasound color flow imaging by Bonnefous as discussed in O. Bonnefous and P. Pesqué, "Time domain formulation of Pulse-Doppler Ultrasound and Blood Velocity Estimation by Cross-Correlation" *Ultrason. Imaging*, vol. 8. pp. 73–85, 1986. This known algorithm operates directly on the received RF (radio frequency) signal, without previous demodulation to baseband.

In U.S. Pat. No. 5,081,994, D. Hassler describes a method applied to the complex demodulated (baseband) signal to avoid aliasing by combining the phase and amplitude of the autocorrelation function.

Hassler uses a simplified algorithm for calculation of the complex correlation function, which gives lower precision (increased variance). In Hassler's method, the correlation phase is calculated by a division followed by inverse tangent. This gives additional ambiguity in the determination of the velocity. In Hassler's method, the correlation phase is not calculated at the lag where the correlation function has its maximum, which gives lower precision for high velocities. Hassler also uses two different approximations for estimating the magnitude of the correlation function, which is different from the mathematical definition. Hassler does not use interpolation in determining the time-shift at peak correlation.

Another approach was used by Ferrara & Algazi as discussed in Ferrara and Algazi, "A new wideband spread target maximum likelihood estimator for blood velocity estimation—Part I: Theory" *IEEE Trans. Ultrason. Ferroelec. and Freq. contr.*, vol. UFFC-38, pp. 1–26, 1991; and Ferrara and Algazi, "The Effect of Frequency Dependent Scattering and Attenuation on the Estimation of Blood Velocity Using Ultrasound" *IEEE Trans. Ultrason. Ferroelec. and Freq. contr.*, vol. UFFC-39, pp. 754–767, 1992. From a stochastic model of the signal from a point scatterer, a maximum likelihood estimate for the velocity was derived, which has the potential to resolve velocity ambiguity. A similar method based on the two-dimensional Fourier transform was proposed by Wilson in K. Miller, *Complex Stocastic Processes*, Addison-Wesley Publishing Company, Inc., 1974, where a velocity spectrum was obtained by summation along straight lines in the 2D Fourier plane. This method is also described in U.S. Pat. No. 4,930,513, referred to as "radial projection in the 2D Fourier plane".

SUMMARY OF THE INVENTION

The present invention comprises a method for velocity estimation based on the complex demodulated Doppler signal in a multigated Doppler, by measuring the time shift of the echoes from pulse to pulse. A related method is described in U.S. Pat. No. 5,081,994 issued to Hassler. The present method differs from Hassler in a number of essential features which are described in detail below, and which gives improved performance compared to Hassler. In addition, a method for receiver noise compensation is included, which enables the use of the method according to the invention under conditions of poor signal-to-noise ratio.

The method can be used for single depth blood flow measurements, color m-mode, and 2D or 3D blood flow imaging. The method is based on the autocorrelation function estimates of the complex demodulated Doppler signal. The contribution to the correlation function from the receiver noise is found by measuring the noise in absence of echo signals, which can be done by turning off the transmitted pulses. The obtained values are subtracted from the correlation estimates before further processing. A limited number of candidates for the true velocity are calculated from the autocorrelation function phase. The method selects the candidate which corresponds to the maximum correlation value, by an interpolation technique.

DETAILED DESCRIPTION OF THE PREFERRED EMBODIMENTS

Figure 1:
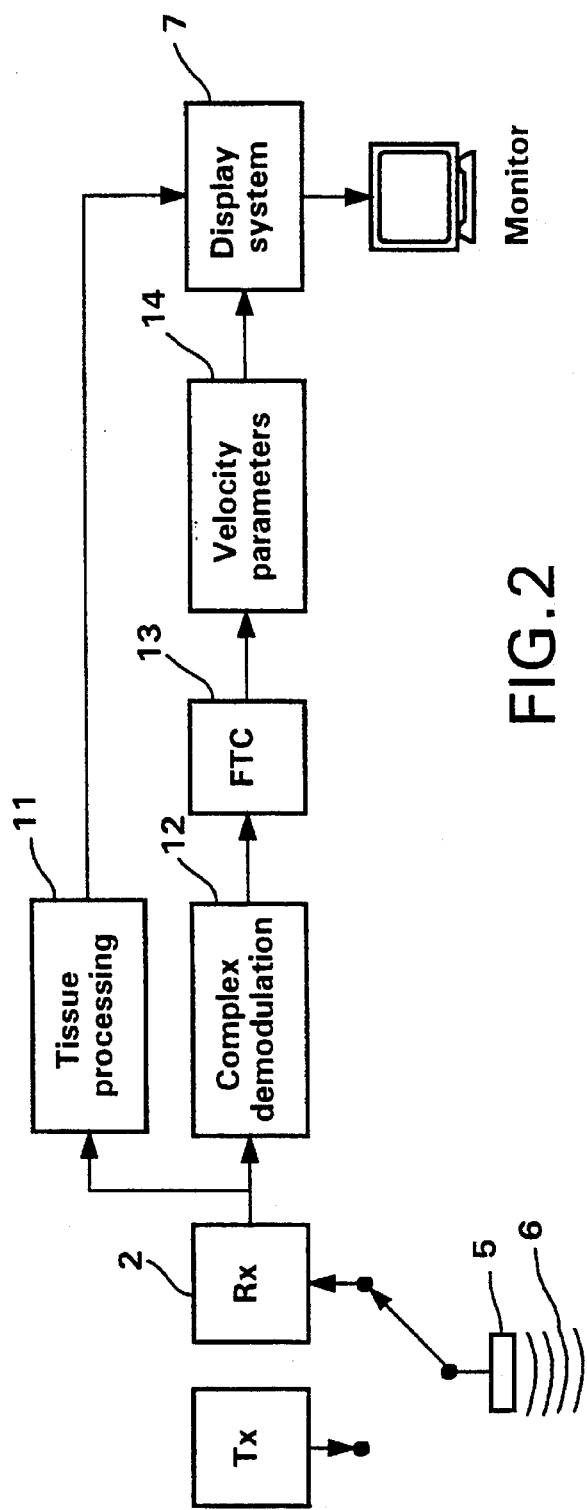
FIG. 1 is an example of a schematic block diagram generally illustrating the main features and functions involved in a complete apparatus for ultrasound color flow imaging, in which the method according to the invention can be implemented.

A block diagram for an ultrasonic Doppler blood flow velocity measurement system where the invention is incorporated is shown in FIG. 1. Usually, the blood flow measurement system is combined with an ultrasonic imaging system utilizing the same transducer, but the invention is also applicable in "stand-alone" Doppler systems. An ultrasonic transducer 5 emits a pulsed ultrasonic beam 6 into the body (not shown). The ultrasonic pulses are backscattered from structures in the body, like blood, to produce echoes which returns to and are detected by the transducer 5, see FIG. 1. From the receiver 2 an arrow indicates the further processing of the echo signals received, first in a complex demodulation stage 12, then in an optional FTC stage 13 to be explained further below, followed by a velocity parameter calculation stage 14. The velocity parameters comprising the three values, power, velocity and velocity spread (see FIG. 2), are calculated for a number of points located in a two-dimensional plane, and combined in the display system 7 with the ultrasonic amplitude image generated in the tissue processing stage 11.

The echo from a scatterer in a distance r from the transducer 5 will be detected with a delay t=2 r/c after pulse transmission, which corresponds to the round-trip time for the ultrasonic pulse to propagate from the transducer to the scatterer and back. The constant c is the speed of sound in human tissue.

For the explanations below the following list of symbols used, may be helpful:

$r_0$ range gate number, $r_0=0, \ldots, M$ $t_0$ pulse number, $t_0=0, \ldots, N-1$ $x(r_0, t_0)$ Multigated, complex Doppler signal from range $r_0$, and pulse number $t_0$ $T_r$ Time increment in radial direction $\omega_0$ Quadrature demodulation angular frequency T Pulse repetition time c speed of sound $R(r,t)$ Autocorrelation estimate of $x(r_0, t_0)$ with radial lag r, and temporal lag t, see equation below $v_{max}$ The maximum blood velocity to be measured is $\pm v_{max}$ (specified by the operator)

$v_{Nyquist}$ Nyquist velocity, i.e. the blood velocity which gives a Doppler shift equal to half the sampling frequency (=1/T)

|z|, phase (z) denotes the magnitude and phase of the complex number z, with real part re{z} and imaginary part im{z} $|z|=\sqrt{(re\{z\}^2+im\{z\}^2)}$; phase(z)=im{log(z)}

Figure 2:
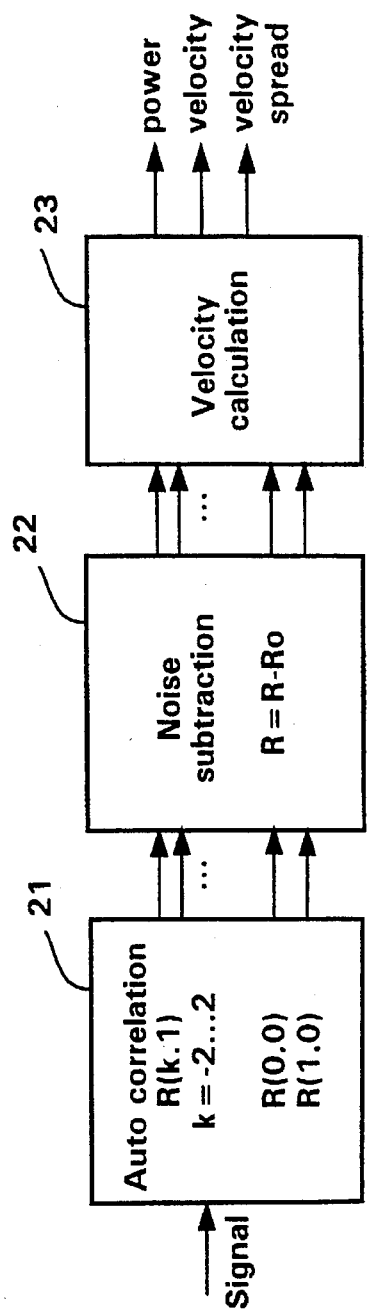
FIG. 2 is a more detailed block diagram on the functional parts of the velocity parameter processor, which is a part of the complete diagram in FIG. 1.

The velocity parameters are calculated from the following set of correlation function estimates (see functional steps or blocks 21, 22, 23 in FIG. 2)

R(0,0), R(1,0), and

R(r,1); r=0, ±1, . . . , ±K which are again calculated in block 21 by a weighted average of the product of the complex signal samples:

$$R(r,t) = \sum_{r_0, t_0} c(r_0, t_0) x(r_0, t_0)^* x(r_0 + r, t_0 + t)$$

where $c(r_0,t_0)$ is an appropriate weighting function. The number of lags in the autocorrelation function K is selected according to the (user defined) velocity range.

$$K = \text{Round}\left\{ \frac{2T v_{max}}{T_r c} + 0.5 \right\}; \quad \text{if } v_{max} > v_{Nyquist}$$

$$K = 0; \quad \text{if } v_{max} <= v_{Nyquist}$$

Figure 3:
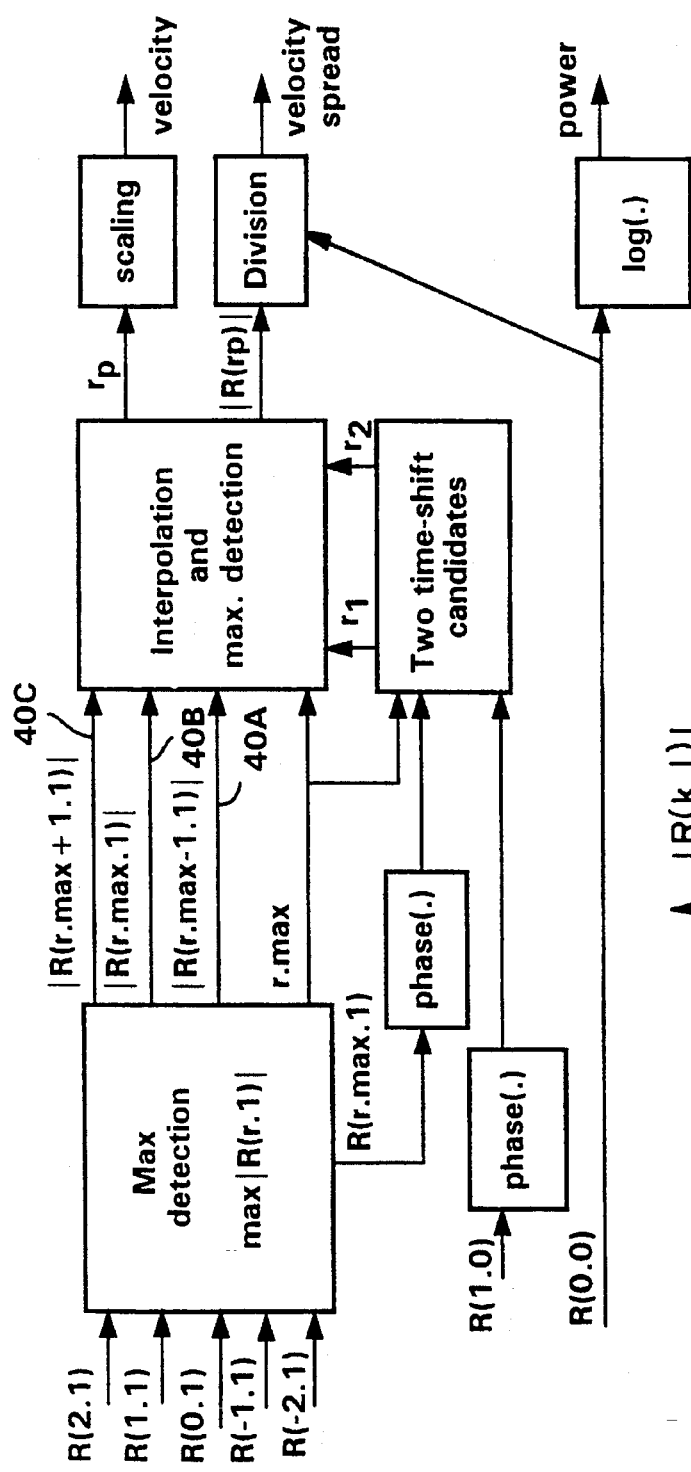
FIG. 3 is a more detailed block diagram on the functional parts of the velocity estimator, which is a part of the diagram in FIG. 2.
Figure 4:
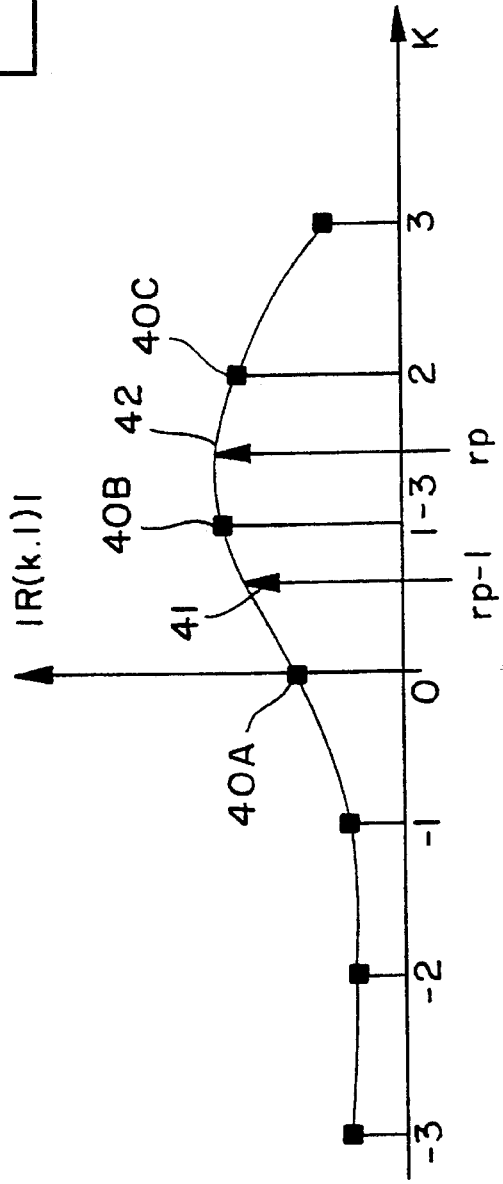
FIG. 4 is an example of the appearance of the magnitude of the complex autocorrelation function.

The calculation of time-shift is performed in three steps, see FIG. 3, FIG. 4:

Step 1. Find the maximum absolute value of the correlation function, i.e. find $r=r_{max}$ which maximize

|R(r,1)|, r=0, ±1, . . . , ±K.

Step 2. Calculate the correlation phase value p with radial lag $r=r_{max}$ p=phase(R($r_{max}$,1))–Δω$r_{max}$ Δω=phase (R(1,0))

The quantity Δω is the deviation of the instantaneous ultrasound center frequency. The calculation of Δω is optional, if it is not used, then Δω is set to zero in the formulas. The possible candidates for echo time-shift are given by $$r_k = \frac{1}{T_r} \frac{p + 2\pi k}{\omega_0 + \Delta\omega}; k=0, \pm 1, \ldots$$

Step 3. By interpolation, the value of |R(r,1)| for any r (not only integer values) can be calculated from |R(k,1)|, k=0, ±1, . . . , ±K. In FIG. 3, only the three correlation values 40A, 40B, and 40C closest to the maximum point $r_{max}$ are used in the interpolation, and only two time-shift candidates 41, 42 in FIG. 4, are located between $r_{max}-1$ and $r_{max}+1$. An example of the appearance of the discrete-time correlation function, and the interpolated values is shown in FIG. 4 as curve 40, which passes through the above three correlation values 40A, 40B, and 40C.

When there are more than one possible candidate, the one which maximize the interpolated magnitude |R($r_k$, 1)| is selected.

This is labeled $r_p$.

The velocity is given by: $v=r_p/T$

A measure of velocity spread:

$$v_s = 1 - \frac{|R(r_p,1)|}{R(0,0)}$$

The velocity spread measure $v_s$ is a qualitative measure of the spread of the velocity around its mean value. When all blood scatterers in the spatial region covered by the ultrasonic beam move with the same velocity, the parameter v, will be close to zero. When the velocity values are equally distributed over the Nyquist velocity range, the spread parameter $v_s$ equals unity.

Receiver noise compensation

The received echo signals are corrupted with additive thermal noise and/or interference noise, generated in the ultrasonic transducer, and/or the receiver amplifier. This gives a bias in the correlation function. By inhibiting the transmission of ultrasonic pulses, the correlation function for the noise in absence of echo signals can be estimated. This noise component in the correlation function is subsequently subtracted from the correlation function of the total signal (including echoes and noise), to give a better estimate of the correlation function of the echo signal.

What is claimed is:

1. A method for determining the velocity of blood flow in one or more spatial positions in a living body utilizing an ultrasonic pulsed wave Doppler system, comprising the steps of:

sequentially transmitting pulsed ultrasonic waves and receiving a corresponding sequence of echo signals;

resolving said echo signals into in-phase and quadrature components constituting a time-discrete complex signal using a chosen demodulation frequency and a chosen sampling frequency;

forming a correlation function of said time-discrete complex signal, said correlation function being represented by a sequence of complex numbers, including magnitude and phase, corresponding to a discrete number of timeshift lags;

determining a maximum magnitude in said correlation function and a corresponding phase value;

calculating a center frequency of said echo signals determining from said corresponding phase value and said center frequency a corresponding set of possible timeshift candidates;

estimating the correlation function magnitude at each possible timeshift candidate by interpolation between the discrete set of timeshift lags in the correlation function; and selecting the one timeshift candidate which corresponds to the maximum correlation magnitude for further calculation of blood flow velocity.

2. The method according to claim 1 further including the step of processing said echo signals by a high-pass filter to reject signals from stationary and slowly moving targets in said living body.

3. The method according to claim 1, further including the step of forming a correlation function for the noise component in a signal received in the absence of ultrasonic echoes, and subtracting said noise component from the correlation function before further processing.

4. The method according to claim 1 further including the step of calculating the velocity spread of said blood flow velocity from said maximum correlation function magnitude.

* * * * *